(12) United States Patent
Hivorel et al.

(10) Patent No.: US 7,579,162 B2
(45) Date of Patent: Aug. 25, 2009

(54) METHOD OF DETECTION IN HOMOGENEOUS PHASE, ESPECIALLY OF PROGESTERONE IN MAMMALS' MILK, AND CORRESPONDING KIT

(75) Inventors: Philippe Hivorel, Lisbonne (PT); Pascal Butty, Fronsac (FR); Francois Deletang, Libourne (FR); Pascal Puig, Castanet Tolosan (FR)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 11/505,436

(22) Filed: Aug. 17, 2006

(65) Prior Publication Data

US 2007/0042449 A1  Feb. 22, 2007

(30) Foreign Application Priority Data

Aug. 18, 2005  (FR) .................................. 05 08609

(51) Int. Cl.
*C01N 33/53* (2006.01)
(52) U.S. Cl. ....................................................... 435/7.8
(58) Field of Classification Search ........................ None
See application file for complete search history.

(56) References Cited

U.S. PATENT DOCUMENTS 4,238,565 A  12/1980  Hornby et al.
4,461,829 A  7/1984  Greenquist
4,496,658 A  1/1985  Kondo et al.
4,931,385 A  6/1990  Block et al.

FOREIGN PATENT DOCUMENTS

GB         2 023 607 A    1/1980

OTHER PUBLICATIONS

Kesler Am Biotechnol Lab 1993:11(2):34-36.*
Yoon et al. J of Immunoassay 1995;16(2):137-153.*
Costantino et al. J of Pharmaceutical Sciences 1998:87(11):1412-1420.*
Dosch et al. "Homogeneous Immunoassay for the detection of Trinitrotoluene (TNT) based on the Reactivation of Apoglucose oxidase using a novel FAD-trinitrotoluene conjugate", Fresenius J Anal Chem 1998, 361:174-178.*
Agrawal et al. "Studies on Peroxidase-catalyzed formation of Progesterone", Steroids, 1982, 40(5):569-579.*
Morris, D. L., et al., "Colorimetric Immunoassays Using Flavin Adenine Dinucleotide as Label," Methods in Enzymology, Academic Press Inc., San Diego, CA vol. 92, No. Part E, 1983 pp. 413-425.

* cited by examiner

*Primary Examiner*—Jon P Weber
*Assistant Examiner*—Bin Shen
(74) *Attorney, Agent, or Firm*—Jacobson Holman PLLC

(57) ABSTRACT

Method for the qualitative and semi-quantitative detection of a ligand in a sample of a medium to be tested, by (1) diluting at least one lyophilized reaction medium in said sample, (2) incubating the sample in order to carry out an immunoenzymatic method, and (3) observing the resulting colouration.

31 Claims, 1 Drawing Sheet

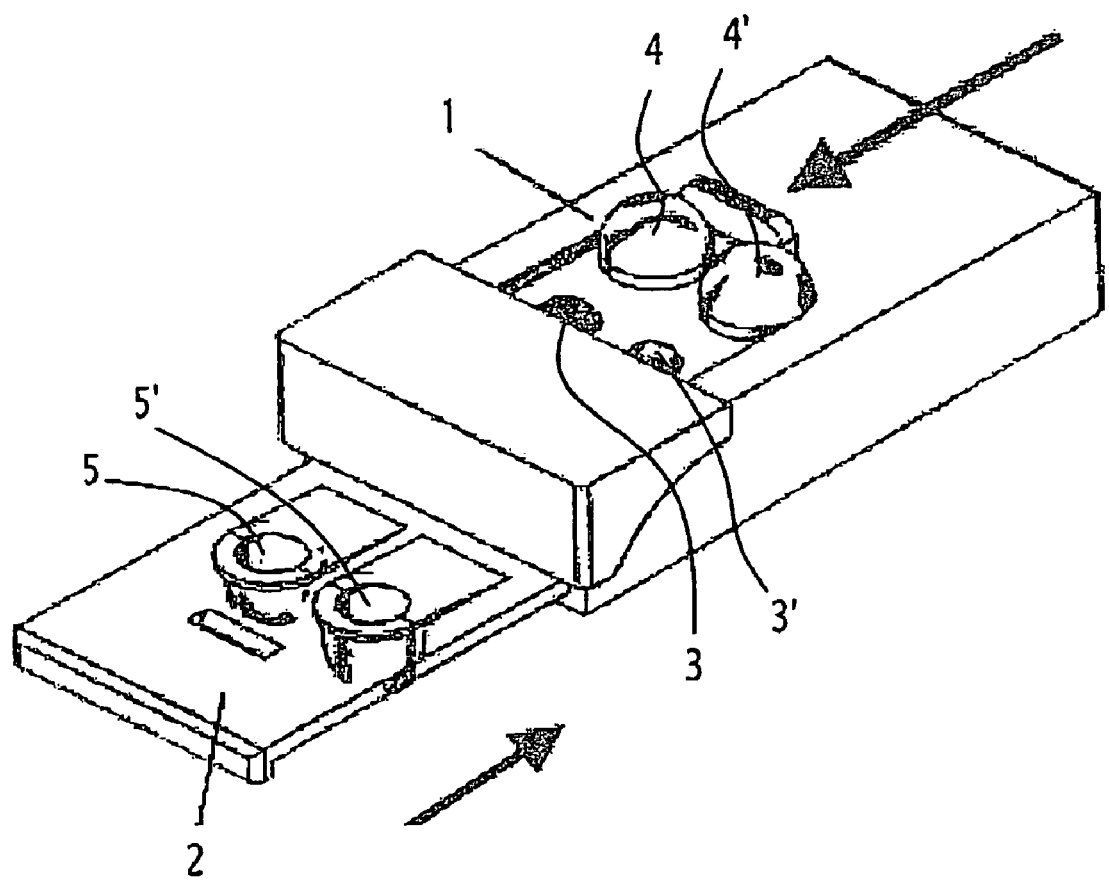

they extracted from the milk sample. The detection kit contains a lyophilised reaction medium and the compounds necessary for carrying out the immunoenzymatic method.

METHOD OF DETECTION IN HOMOGENEOUS PHASE, ESPECIALLY OF PROGESTERONE IN MAMMALS' MILK, AND CORRESPONDING KIT

TECHNICAL FIELD

The invention relates to a method and a kit for the rapid detection of a ligand in a sample of a medium to be tested. The detection may b in particular qualitative or semi-quantitative.

BACKGROUND TO THE INVENTION

A number of immunoenzymatic or immunochemical methods have been developed to date for detecting the presence of ligands in media. The ELISA (Enzyme-Linked ImmunoSorbent Assay) method consists in detecting antigenic ligands by means of specific antibodies conjugated to an enzyme (phosphatase, peroxidase, etc.). The RIA (Radio-Immuno Assay) method consists in analysing an antigen using a radioactive antigen, the antigen to be analysed displacing the bond between the radioactive antigen and the antibody in proportion to its concentration. The ARIS (Apoenzyme Reactivation Immunoassay System) method, described in FR 2 429 258 or U.S. Pat. No. 4,238,565, consists in detecting a ligand by using a ligand conjugated to a prosthetic group and using specific antibodies, the ligand to be analysed displacing the bond between the conjugate and the antibody in proportion to its concentration, the conjugate in free form then activating an apoenzyme which produces a colour reaction directly or indirectly.

Those methods are carried out especially for detecting molecules present in biological media. By way of example, methods have been developed for detecting progesterone concentration. European Patent Application EP 0 671 006 dated 26 Nov. 1993 relates to an ELISA method for detecting progesterone in cows' milk. British Patent Application GB 2 354 069 dated 8 Apr. 1999 relates to a method for detecting the progesterone concentration in cows' milk taken 4, 5 or 6 days after insemination, by carrying out ELISA or RIA methods. The ARIS method, on the other hand, has not hitherto been applied for detecting progesterone.

Those methods, as conducted at present, exhibit numerous disadvantages. They generally require solid supports with one or several reagents immobilized on them and several steps to be carried out, especially steps of incubation, washing and detection of the reaction (for example U.S. Pat. Nos. 4,461,829, 4,931,385, 4,496,658). This procedure frequently requires the use of specific equipment within the context of an analytical laboratory, especially for measuring the radioactivity, for measuring the enzymatic reaction or for measuring the colour reaction. Finally, those methods can be carried out only by the person skilled in the art. The way in which those methods are carried out at present is therefore not suitable for the simple, reliable and rapid detection of a ligand in a medium.

SUMMARY OF THE INVENTION

The present invention resolves the disadvantages inherent in the implementation of the methods described in detail hereinbefore and is suitable for the simple, reliable and rapid detection of a ligand in a medium.

DESCRIPTION OF THE INVENTION

The invention relates to a method for the rapid qualitative and semi-quantitative detection of a ligand in a sample of a medium to be tested, by (1) diluting at least one lyophilised reaction medium in said sample, (2) incubating the sample in order to carry out an immunoenzymatic method, and (3) observing the resulting colouration.

Particularly advantageously, the invention relates to said detection method in which observation of the resulting colouration is carried out with the naked eye.

Said method is simple and rapid to use because it does not require a large number of incubation and/or washing steps and because no expertise in this technical field is required to carry it out. Said method does not require either the use of solid supports such as strip, reaction wells and the like with one or several reagents immobilized on them. In fact, said method only requires the sample of the medium to be tested (referred to hereinafter as the sample) to be mixed with the lyophilised reaction medium (media), the mixture(s) to be incubated and the resulting colouration to be observed, optionally with the naked eye. This rapid, simple and reliable use of said method is made possible by the use of reaction media prepared in the form of lyophilised reaction media. Said lyophilised reaction media comprise especially the compounds necessary for carrying out the immunoenzymatic method (referred to hereinafter as the reaction compounds) and a vector matrix comprising at least one compound acting as a vector for the reaction compounds (referred to hereinafter as the vector compound).

According to a particular embodiment, said lyophilised reaction medium is obtained by (1) mixing the reaction compounds with a matrix solution comprising at least one vector compound, (2) forming solid reaction media by immersing small volumes of said mixture in liquid nitrogen, and (3) forming lyophilised reaction media by sublimation of the solid reaction media by lyophilisation in vacuo.

The lyophilised reaction media obtained according to said process are solid matrices of spherical shape and have a diameter of several millimetres and a weight of several micrograms. Their diameter is preferably less than 20 mm. Very preferably, the diameter is less than 5 mm.

The lyophilised reaction media are highly stable since they can be stored for several years at 4° C. and for several months at ambient temperature in an environment without light and without moisture. Preferably, the media are stable, in the absence of light and moisture, for at least 18 months at 4° C. and for at least 2 months at ambient temperature.

The media are diluted completely and rapidly in a liquid medium, especially the medium sample to be tested. According to the invention, "dilution" means that the lyophilised reaction media disperse in the liquid sample; said media may completely or partially dissolve in this liquid sample. Thus, the vector or vectors may dissolve in all or part in the liquid sample. The reagents are in homogeneous phase with the liquid sample to be tested. Preferably, the lyophilised reaction media dissolve in the liquid sample of medium to be tested, especially in less than five minutes, preferably in less than one minute and, very preferably, in from 10 to 30 seconds.

The stability and dissolution properties of the lyophilised reaction media are closely linked to the nature and quantity of the vector compounds used. Advantageously, said vector compounds are so selected that they ensure good stability of the lyophilised reaction media and do not affect the quality and/or rapidity of the immunoenzymatic method. Said vector compounds are selected in dependence upon the ligand to be analysed and the media to be tested.

The vector compounds are preferably selected especially from the glucidic compounds. Very preferably, the glucidic compounds are selected from simple or complex soluble sugars and especially monosaccharides (oses, aldoses, ketoses, glucose, etc.) and polysaccharides (disaccharides, oligoholosides, heterosides) of natural or synthetic origin. Glucose polymers are examples of useful polysaccharides. More preferably, the vector compounds are trehalose, dextran, mannitol and bovine serum albumin. Combinations of two or three of these cited compounds, or the use of only one, are within the scope of the invention. More preferably, the vector compounds correspond to from 60 to 95% by volume of the lyophilised reaction media. Indeed, it may be preferable to use the vector compounds in reduced proportions in order to limit the interactions between the vector compounds and the reaction compounds and/or the compounds present in the sample of medium to be tested.

In particular, the immunoenzymatic method carried out in said detection method is the inactivated apoenzyme reactivation method (or ARIS method). That method comprises the steps of bringing the sample of said medium to be tested into contact with at least one lyophilised reaction medium comprising (1) a conjugate formed by covalently bonding a prosthetic group to a ligand, (2) a monoclonal antibody that binds in a specific and competitive manner to the ligand to be analysed or to the conjugate, and (3) an inactivated apoenzyme activatable by binding to the prosthetic group of the conjugates that are not bound to a monoclonal antibody; said activated apoenzyme catalysing, directly or indirectly, a colour reaction proportional to the quantity of ligand to be analysed that is present in the sample of medium to be tested. More preferably, the monoclonal antibody binds specifically to the ligand bound to the conjugate.

The immunoenzymatic method of inactivated apoenzyme reactivation is based on the competition between the ligand to be analysed and the ligand bound to the conjugate (referred to hereinafter as the conjugated ligand) for specific binding to the monoclonal antibody.

The apoenzyme corresponds to the protein part of holoenzymes that provides for the fixing of the substrate and ensures the specificity of the enzymatic reaction. The prosthetic group corresponds to a non-protein enzymatic cofactor which fixes in a non-covalent manner to the apoenzyme; the prosthetic group is indispensable for the enzymatic reaction. In the absence of fixing of the prosthetic group to the apoenzyme, said apoenzyme is in the inactivated form (referred to hereinafter as the inactivated apoenzyme) and no catalytic reaction takes place. By contrast, when the prosthetic group is bound to the apoenzyme, the apoenzyme is activated (referred to hereinafter as the activated apoenzyme or holoenzyme) and the substrate is catalysed. Moreover, in contrast to the ELISA method, for example, the inactivated apoenzyme is in free form and is therefore not conjugated to other molecules such as monoclonal antibodies. Among the holoenzymes (prosthetic group), mention may be made of glucose oxidase (FAD).

The ligand corresponds to any type of molecule that can be recognised specifically by a monoclonal antibody (referred to hereinafter as the ligand to be analysed). Said molecule is preferably of small size. In the case of biological media, the ligands are especially haptens, peptides, oligopeptides or polypeptides of small size, protein fragments, glycoproteins, lipoproteins and steroids. The ligands can belong to different classes of molecules, especially antigens, hormones, vitamins, metabolites and antibiotics. The molecules can be endogenous or exogenous. Exogenous molecules can be especially medicament molecules or molecules of bacterial, viral or parasitic origin.

The conjugate comprises a prosthetic group bound directly or indirectly to the ligand or to its analogue by a covalent bond. The covalent bond can be obtained by the use of an intermediate compound bound to the prosthetic group and to the ligand. The bond of the prosthetic group to the ligand does not alter the specificity and affinity of the bond between the ligand and the monoclonal antibody, on the one hand, or, on the other hand, the specificity and affinity of the non-covalent bond between the prosthetic group and the apoenzyme Alternatively, the ligand to be analysed can be the prosthetic group of the apoenzyme. In that case, the conjugate/conjugated ligand corresponds to the prosthetic group in modified or unmodified form.

The monoclonal antibody must recognise the ligand to be analysed and the conjugated ligand with specificity and affinity. Recognition of the conjugated ligand by the monoclonal antibody will generally induce conformational modifications of the conjugate and/or a steric hindrance which prevents the bond between the prosthetic group and the inactivated apoenzyme. Furthermore, the antibodies are not fixed to an inert support; they are in free form, since they are not conjugated to molecules such as enzymes and they do not participate directly in the colour reaction.

When the conjugated ligand is bound to the antibody, the prosthetic group of the conjugate is unable to bind in a specific and non-covalent manner to the inactivated apoenzyme, said apoenzyme then being unable to catalyse the substrate. After dilution of said at least one lyophilised reaction medium in the sample of medium to be tested, the lower the rate of binding of the monoclonal antibody to the conjugated ligand, the higher the quantity of ligand to be analysed in the sample. As the corollary, the lower the rate of binding of the monoclonal antibody to the conjugated ligand, the higher the activation of the inactivated apoenzyme and the more intense the resulting colour reaction.

Said colour reaction is preferably obtained by catalysis of at least one substrate by the activated apoenzyme to give at least one reagent, said reagent being necessary for the activation of a second enzyme which degrades a chromogenic compound proportionally to the quantity of reagent formed and, indirectly, proportionally to the quantity of ligand to be analysed that is present in the sample of medium to be tested.

The intensity of the colour reaction (which is also referred to as the colouration) will be dependent upon the quantity of chromogenic compound catalysed by the second enzyme, the quantity of chromogenic compound catalysed being proportional to the quantity of reagent produced by the apoenzyme, and the quantity of reagent produced being directly correlated with the rate of activation of the apoenzyme and therefore with the rate of fixing of the prosthetic group to the inactivated apoenzyme.

Said chromogenic compound can be a non-coupled chromogenic compound or a chromogenic compound coupled to a cofactor (referred to hereinafter as coupled chromogenic compound). In the case of a coupled chromogenic compound, the presence of the cofactor will be indispensable for the reaction catalysed by the second enzyme.

Among the enzymes which can be used as the second enzyme, mention may be made of the peroxidases.

Among the non-coupled chromogenic compounds, mention may be made of tetramethylbenzidine (TMB) and 2,2'-azino-bis-[3-ethylbenzothiazoline-6-sulfonic acid] (ATBS). Among the coupled chromogenic compounds, mention may be made of 3,5-dichloro-2-hydroxybenzenesulfonate (DHSA) coupled to 4-aminoantipyrine (4-AP), 3-methyl-2-benzothiazoline hydrazone hydrochloride (MBTH) coupled to dimethylaminobenzaldehyde (DMAB), MBTH coupled to DMAB and to 4-AP, DMAB coupled to 4-AP.

The colour reaction is obtained by catalysis of a non-coupled or coupled chromogenic compound by a peroxidase enzyme in the presence of hydrogen peroxide produced by the activated apoenzyme. The presence of hydrogen peroxide is indispensable for the catalysis of the chromogenic compound by the peroxidase. Furthermore, said catalysis is proportional to the quantity of hydrogen peroxide produced, and the resulting colouration is therefore proportional to the quantity of chromogenic compound catalysed and therefore to the quantity of hydrogen peroxide produced. The resulting colouration is specific to each coupled or non-coupled chromogenic compound used. DHSA coupled to 4-AP develops a pink to red colouration. TMB develops a blue colouration. ABTS develops a green colouration. MBTH coupled to DMAB develops a violet colouration. MBTH coupled to DMAB and to 4-AP develops a violet-pink colouration. DMAB coupled to 4-AP develops a violet-pink colouration.

Binding of the prosthetic group to the inactivated apoenzyme, and therefore activation of the apoenzyme, are possible only if the conjugate is in free form. The binding of the antibodies to the conjugated ligands is dependent upon the quantity of ligand to be analysed, said antibodies having great specificity and a high degree of affinity both for the ligand to be analysed and for the conjugated ligand. In the absence of ligand to be analysed, the very large majority of the conjugates are bound to the antibodies. Conversely, in the presence of a large quantity of ligand to be analysed, the very large majority of the conjugates are in free form. Activation of the apoenzyme is directly proportional to the free conjugate/bound conjugate ratio and therefore to the quantity of ligand to be analysed.

The higher the quantity of ligand in the sample, the higher the free conjugate/bound conjugate ratio and the more intense the colour reaction. By contrast, the smaller the quantity of ligand in the sample, the lower the free conjugate/bound conjugate ratio and the weaker the colour reaction.

Also preferably, said lyophilised reaction medium comprises at least one neutralising compound.

The media to be tested are complex media comprising a large number of different compounds. Some of those compounds can interact with the reaction compounds and/or the vector compounds and/or the ligand to be analysed and/or the products of the enzymatic reactions. Such interactions can modify the rapidity and reliability of the detection method. In order to limit the effects of such compounds, it is preferable to add neutralising compounds to the lyophilised reaction medium.

It is possible to prepare the reaction compounds in a single lyophilised reaction medium, but the reaction compounds are preferably prepared in at least two different lyophilised reaction media, (1) the first lyophilised reaction medium comprising especially the inactivated apoenzyme, the monoclonal antibody, the cofactor for the chromogenic compound, at least one neutralising compound and, optionally, the substrate, and (2) the second lyophilised reaction medium comprising especially the second enzyme, the chromogenic compound, the conjugate and, optionally, the substrate Alternatively, the reaction compounds are prepared in at least two different lyophilised reaction media, (1) the first lyophilised reaction medium comprising especially the inactivated apoenzyme, the monoclonal antibody, the non-coupled chromogenic compound, at least one neutralising compound and, optionally, the substrate, and (2) the second lyophilised reaction medium comprising especially the second enzyme, the conjugate and, optionally, the substrate.

The use of at least two different lyophilised reaction media is preferable in order to optimise the detection method; reaction compounds being able to react with one another by simple contact. Accordingly, it is preferable for the inactivated apoenzyme and the conjugate not to be in the same lyophilised reaction medium in order to avoid activation of the inactivated apoenzyme before the sample is added. Furthermore, it is preferable for the conjugate and the antibodies not to be in the same medium in order to avoid binding thereof before the sample is added. In addition, it is preferable for the second enzyme and the non-coupled chromogenic compound not to be in the same medium in order to avoid catalysis of the chromogenic compound before the sample is added. Alternatively, it is preferable for the second enzyme and the coupled chromogenic compound, on the one hand, and the cofactor for the chromogenic compound, on the other hand, not to be in the same medium in order to avoid catalysis of the chromogenic compound before the sample is added.

Alternatively, when at least two different reaction media are used, said media can be diluted in the sample of medium to be tested concomitantly or sequentially. The sequential dilution of the lyophilised reaction media is preferable so that said at least one neutralising compound neutralises the compounds present in the sample that are capable of altering the implementation of the detection method. Furthermore, in cases where compounds present in the medium to be tested are capable of degrading and/or reacting with the products formed during the reaction catalysed by the activated apoenzyme, it is preferable for the substrate to be placed in the second lyophilised reaction medium so that the enzymatic reaction is not initiated until the compounds present in the medium to be tested have been neutralised.

According to a particular embodiment, said detection method further comprises carrying out a reference method by (1) diluting at least one reference lyophilised reaction medium, without monoclonal antibodies, in a second sample of medium to be tested, (2) incubating the second sample, (3) observing the resulting reference colouration, and optionally (4) comparing said reference colouration and the colouration obtained with the first sample. The resulting reference colouration preferably corresponds to a given concentration of the ligand in the medium to be tested.

The dilution and then incubation of at least one reference lyophilised reaction medium in a second sample of medium to be tested allow a reference detection method to be carried out and a reference colour reaction to be obtained. To that end, said at least one reference lyophilised reaction medium does not contain monoclonal antibodies. In the absence of monoclonal antibodies, the conjugate is in free form and the prosthetic group binds to the inactivated apoenzyme. Activation of the inactivated apoenzyme and the intensity of the resulting reference colouration are maximum and independent of the concentration of ligand present in the medium to be tested. This is a positive control which facilitates comparison and interpretation with the naked eye of the calorimetric results obtained between the first and second samples. In fact, said at least one reference reaction medium can be standardised by adjusting the quantity of conjugate so that the resulting reference colouration corresponds to a known ligand concentration. In order to allow valid comparison of the colouration obtained with the first sample and the reference colouration, the first and second samples are obtained from the same aliquot and/or undergo the same treatment. Furthermore, the detection method and the reference method are carried out simultaneously and under the same experimental conditions.

The reaction compounds are preferably prepared in at least two different reference lyophilised reaction media, (1) the first reference lyophilised reaction medium comprising especially the inactivated apoenzyme, the cofactor for the chromogenic compound, at least one neutralising compound and, optionally, the substrate, and (2) the second reference lyophilised reaction medium comprising especially the second enzyme, the coupled chromogenic compound, the conjugate and, optionally, the substrate.

The medium to be tested can vary in terms of its nature. It can be a natural medium or a synthetic medium.

The medium to be tested is preferably a biological medium, said medium being tested as such or being tested after previously being treated, especially diluted. Alternatively, it can be a treated or untreated liquid biological medium or a liquid biological medium obtained from a solid medium (tissue, etc.) by application of a specific treatment (dissolution, extraction, etc.).

More preferably, said biological medium is taken from an animal or from a human being by known methods. Alternatively, said animal can be a productive animal or a companion animal. Productive animals include especially pigs, bovines, ovines, caprines, camelidae, buffaloes, lagomorphs and fish for breeding. Among them, the most preferred productive animals are the mammals. Companion animals include especially dogs, cats, horses, fish and reptiles.

More preferably, said biological medium is selected from saliva, milk, urine, sweat, lachrymal fluid, mucosal secretions, plasma, amniotic fluid, cephalo-rachidian liquid, water and serum. Very preferably, said biological medium is milk.

The ligand to be analysed in said biological medium is selected from haptens, peptides, oligopeptides or polypeptides of small size, protein fragments, glycoprotein fragments, lipoprotein fragments and steroid fragments. The ligands can belong to different classes of molecules, especially antigens, hormones, vitamins, metabolites and antibiotics. The molecules can be endogenous or exogenous. Exogenous molecules can be especially medicament molecules or molecules of bacterial, viral or parasitic origin.

A large number of ligands can be analysed by this method. To that end, it is necessary to have available, on the one hand, a conjugate comprising the prosthetic group bound covalently to said ligand or to an analogue and, on the other hand, a compound that recognises the conjugated ligand in a specific and non-covalent manner. The compound that recognises the ligand to be analysed, or conjugate, is not necessarily a monoclonal antibody. It may be a molecular receptor.

Said ligand is preferably a hormone. Very preferably, said hormone is progesterone in free form. Determination of the progesterone concentration in a mammal's milk, e.g. a cow is useful for determining the phase of the sexual cycle of said mammal (ovulation, etc.). In addition to the cow, the invention applies especially also to the productive animals, more particularly to the productive mammals mentioned above, for example the sow, the ewe, the goat.

Alternatively, said ligand is an antibiotic, a residue thereof or a degradation product thereof. Determination of the concentration of antibiotics in milk, e.g. cows' milk or in another biological medium is useful especially when the animal is an animal whose milk and/or meat is intended for human or animal consumption.

Alternatively, said ligand is an antibody. Determination of the concentration of antibodies in the blood and/or serum is useful for assessing the effectiveness of a vaccination carried out, for example, on poultry.

Alternatively, said ligand is a biological tracer. Said biological tracer is preferably flavin adenine dinucleotide (FAD). Determination of the concentration of FAD in the blood, previously treated in order to break open the cells and free the FAD into the medium, is useful for identifying animals suffering from chronic mastitis. Likewise, determination of the concentration of FAD in the urine is useful for identifying animals suffering from a chronic urinary infection.

Alternatively, said ligand is a protein or a protein fragment specific to a given physiological and/or pathological state. Among these proteins, one may mention the pregnancy-specific proteins (Butler et al. "Detection and partial characterization of two bovine pregnancy-specific protein", 1982, Biol. Reprod., 26, 925-933, Sasser et al. "Detection of pregnancy by radioimmunoassay of a novel pregnancy specific protein in serum of cow and a profile of serum concentration during gestation", 1986, Biol. Reprod., 35: 936-942) and the pregnancy-associated proteins such as for example the PAG (Pregnancy Associated Glycoprotein; Zoli et al. "Purification and characterization of a bovine pregnancy associated glycoprotein", 1991, Biol. Reprod., 45, 1-10), the pregnancy seric protein PSG60 or still the bovine pregnancy-associated protein bPAG (bovine Pregnancy Associated Glycoprotein). Preferably, said protein is PBPS (Pregnancy-Specific Proteins B) which is a protein specific to pregnancy. Determination of the concentration in the blood, serum and/or milk is useful for determining a gestational state.

Alternatively, said ligand is all or part of a pesticide or a degradation product thereof. Determination of the concentration in the drinking water is useful for determining the level of pollution of said water.

Alternatively, said ligand is all or part of an intoxicating substance or a degradation product thereof. Detection of such substances in the blood and/or saliva is useful for establishing an urgent diagnosis.

In a particular embodiment, the apoenzyme is an oxidase that catalyses the substrate in the presence of the prosthetic group to produce at least hydrogen peroxide.

The apoenzyme is preferably apo-glucose oxidase (referred to hereinafter as apo-GOD), the prosthetic group is flavin adenine dinucleotide (referred to hereinafter as FAD) and the substrate is glucose. Glucose, the substrate of apo-GOD, corresponds to a vector compound and to a reaction compound when it is incorporated into the lyophilised reaction medium (media).

In addition, the second enzyme is horseradish peroxidase (referred to hereinafter as HRP) and the chromogenic compound is 5-dichloro-2-hydroxybenzenesulfonate coupled to 4-aminoantipyrine.

HRP is active only in the presence of hydrogen peroxide. Furthermore, that enzyme catalyses the chromogenic compound DHSA only in the presence of 4-AP. Catalysis of DHSA coupled to 4-AP develops a pink to red colouration.

In addition, the ligand to be analysed in said biological medium is progesterone in free form.

Hormones are involved in the regulation of a large number of physiological states. Accordingly, the analysis of hormones in biological fluids generally permits the precise determination of a physiological or pathological state. The analysis of progesterone in free form (also referred to hereinafter as P4) in mammals' milk permits a precise determination of the cyclicity state (also referred to as the sexual cycle) or the gestational state. Accordingly, for example in a cow, the level of P4 in the milk will vary in dependence upon the phase of the cyclicity state. The reproductive cycle of a cow in the absence of fertilisation has an average duration of 21 (to 24 days). The cycle is divided into four phases. The first phase, called pro-oestrus, coincides with the pre-ovulatory follicular phase and lasts from 2 to 3 days. This first phase corresponds to the development of the follicles, to maturation and growth of secondary follicles, and to the obtainment of a dominant follicle called the Graafian follicle. The second phase, called oestrus or heat, lasts on average from 0.5 to 2 days, during which the dominant follicle secretes a large number of oestrogens, inducing behavioural manifestations (or heat) with acceptance of mounting and covering. This is the period of sexual receptiveness and is followed by ovulation ("laying" of the ovocyte outside the follicle) about 30 hours after the start of heat, followed by the development of the corpus luteum from the follicle and migration of the ovule through the Fallopian tubes for approximately 6 hours then its final location in the ampulla of the Fallopian tubes, where the ovule is fertilisable for 2 to 3 hours. The third phase, or metoestrus, lasts from 3 to 5 days and corresponds to the maturation of the corpus luteum. The fourth phase, or dioestrus, lasts from 13 to 14 days and corresponds to the secretion of progesterone by the active corpus luteum, followed by regression of the corpus luteum.

The progesterone secreted by the corpus luteum circulates in the blood and then becomes concentrated in the milk. By analysing this progesterone, it is possible to observe the fluctuations in the quantity of progesterone produced during the sexual cycle. During heat, the concentration of P4 in the milk is close to 0 ng/ml. Starting at ovulation, the corpus luteum will secrete progesterone, the concentration of which in the milk will gradually increase until it reaches 5 ng/ml or even 9 ng/ml. If the ovule is not fertilised, the corpus luteum regresses and the concentration of progesterone falls. If the ovule is fertilised, the concentration of P4 remains stable and increases during gestation.

As the corollary, the monoclonal antibody is an anti-progesterone 2B5 antibody produced by the cell line deposited on 17 Mar. 2005 with the Collection Nationale des Cultures de Microorganismes, Institut Pasteur, 28, rue du Dr Roux, 75724 Paris Cedex 15, France, under number 1-3403 in the name of CBVA 2B5 antibodies are monoclonal antibodies of the IgG1 immunoglobulin type. 2B5 antibodies have a high affinity and a high degree of specificity for progesterone in free form and for progesterone bound to the conjugate. By contrast, said antibodies do not recognise steroid molecules similar to progesterone and, especially, 5α-pregnone-3,20-dione; pregnenolone; 11α-deoxy-corticosterone; 5α-androstone-3,17-dione; 5β-androstone-3,17-dione; corticosterone; atiocholanol; oestradiol; testosterone; cortisol and oestrone. This strict affinity for conjugated or non-conjugated progesterone, and not for related molecules, guarantees the sensitivity and specificity of the method carried out.

Finally, the lyophilised reaction medium further comprises ascorbate oxidase.

In order to optimise the detection of progesterone in cows' milk, it is preferable to incorporate ascorbate oxidase into the lyophilised reaction medium as the neutralising compound. Indeed, milk naturally contains a high concentration of ascorbic acid. Ascorbic acid can disrupt the detection method by degrading the hydrogen peroxide formed and the chromogenic compound. The addition of ascorbate oxidase therefore catalyses the ascorbic acid and allows optimum analysis of the ligand to be analysed.

The reference colouration obtained preferably corresponds to a concentration of between about 1 and about 3 ng/ml of progesterone in a female mammals' milk, for example about 2 ng/ml of progesterone in cows' milk.

It is valuable to standardise the reference lyophilised reaction medium (media) so that the resulting reference colouration corresponds to a fixed threshold concentration of progesterone, said concentration being correlated with a given physiological state, in the present case oestrus.

Standardising the reference method so that the reference colouration corresponds to a concentration of between about 1 and about 3 ng/ml, e.g. about 2 ng/ml allows it to be determined whether the cow is in heat. This value is said to be the reference value or threshold value. Indeed, if the intensity of the colouration of the first incubated sample is less than the reference colouration, the milk tested has a progesterone concentration lower than the reference value (threshold value) and the cow is in heat. If, on the other hand, the intensity of the colouration of the first incubated sample is greater than or equal to the reference colouration, the milk tested has a progesterone concentration greater than the reference value and the cow is not in heat.

It has been said that for the cow this reference value may be set at a value between about 1 and about 3 ng/mL, for example the value 2 ng/mL. It is possible to choose the threshold value that is recommended by the professionals according to the mammal species.

According to another object, the present invention relates to a kit for the qualitative and semi-quantitative detection of a ligand in a sample of a medium to be tested, which kit comprises at least one reaction medium comprising (1) a conjugate formed by covalently bonding a prosthetic group to a ligand, (2) a monoclonal antibody that binds in a specific and competitive manner to the ligand to be analysed or to the conjugated ligand, (3) an inactivated apoenzyme activatable by binding to the prosthetic group of the conjugates that are not bound to a monoclonal antibody, (4) a chromogenic compound, (5) a second enzyme that catalyses said chromogenic compound proportionally in the presence of at least one reagent produced by the activated apoenzyme, said catalysed chromogenic compound generating a colouration proportional to the quantity of ligand to be analysed that is present in the sample of medium to be tested, and optionally a substrate catalysable by the activated apoenzyme, optionally a cofactor for the chromogenic compound and optionally one or more neutralising compounds.

The kit, which is intended for the qualitative and semi-quantitative detection of progesterone in free form in a sample of cows' milk, preferably comprises at least one lyophilised reaction medium comprising especially inactivated apo-glucose oxidase, the FAD-progesterone conjugate, the anti-progesterone 2B5 monoclonal antibody produced by the cell line I-3403, ascorbate oxidase, horseradish peroxidase, the chromogenic compound 5-dichloro-2-hydroxybenzenesulfonate, the cofactor 4-aminoantipurine and glucose.

Said kit very preferably comprises (1) glucose, (2) a first lyophilised reaction medium comprising inactivated apo-glucose oxidase, 4-amino-antipurine (cofactor for the chromogenic compound), ascorbate oxidase and the anti-progesterone 2B5 monoclonal antibody produced by the cell line I-3403, and (3) a second lyophilised reaction medium comprising horseradish peroxidase, the chromogenic compound 5-dichloro-2-hydroxybenzenesulfonate and the FAD-progesterone conjugate.

More preferably, said kit comprises (1) glucose, (2) a first reference lyophilised reaction medium comprising inactivated apo-glucose oxidase, 4-aminoantipurine and ascorbate oxidase, and (3) a second reference lyophilised reaction medium comprising horseradish peroxidase, the chromogenic compound 5-dichloro-2-hydroxybenzenesulfonate and the FAD-progesterone conjugate.

It is immaterial whether the glucose is incorporated into the first lyophilised reaction medium and/or into the second lyophilised reaction medium and/or is not incorporated into said lyophilised reaction media. Likewise, the glucose is incorporated either into the first reference lyophilised reaction medium and/or into the second reference lyophilised reaction medium and/or is not incorporated into said reference lyophilised reaction media.

According to another object, the present invention relates to a process for the preparation of a purified, stabilised and inactivated apo-GOD from a GOD bound to FAD, by (1) purification and removal of contaminants, (2) stabilisation by reaction with dimethyl adipimidate, and (3) inactivation by removal of the prosthetic group FAD.

The preparation of a purified, stabilised and inactivated apo-GOD is preferable to obtain a reliable and accurate detection method.

The purified apo-GOD is obtained by removing the contaminants and inactivating the catalase, the enzyme which catalyses hydrogen peroxide. Removal of the catalase is indispensable because it would disrupt the results obtained. In fact, when the lyophilised reaction media are dissolved with the sample of medium to be tested, the inactivated apo-GOD is activated by fixing of the FAD and catalysis of the glucose in the presence of oxygen to produce gluconolactone and hydrogen peroxide. The hydrogen peroxide then acts as the reagent for the horseradish peroxidase, which catalyses the chromogenic compound. If the lyophilised reaction medium comprises catalase, it catalyses the hydrogen peroxide and the colour reaction produced by the HRP is less intense than expected. Preferably, the irreversible inactivation of the catalase is effected using sodium bisulfite, and the removal of the contaminants is effected by filtration.

The apo-GOD is stabilised by the grafting of dimethyl adipimidate (referred to hereinafter as DMA) by a covalent bond, said grafting compensating for the intrinsic instability of apo-GOD in the absence of FAD. The non-cleavable covalent bond having six atoms forms between the imidoester groups of DMA and the free amine functions of the apo-GOD.

The apo-GOD is inactivated by removal of the FAD. FAD is a prosthetic group which binds non-covalently to the inactivated apo-GOD. That bond induces conformational modifications to the apo-GOD, bringing about its activation. Preferably, the removal of FAD is obtained by dissociation of the apo-GOD and FAD in the presence of adenine dinucleotide diphosphate (referred to hereinafter as AMP) and glycerol, then by filtration.

According to another object, the present invention relates to a process for the preparation of a P4FAD conjugate by (1) activating progesterone by binding to hemisuccinate (HNS) to give a P4-HNS, then (2) binding the P4-HNS with $N^6$-(6-aminohexyl)-FAD (AHFAD) to give P4-FAD.

According to another object, the present invention relates to the P4-FAD conjugate.

In the preferred embodiment, a kit is used to determine whether the female mammal, for example the cow is in heat.

According to a preferred embodiment, the kit used, which is miniaturised and is for a single use, comprises a fixed zone (1) and a slide (2) which is able to slide into said fixed zone. The fixed zone has four compartments (3), (3') and (4), (4') each containing one of the four lyophilised reaction media. The four lyophilised reaction media are therefore stored separately in moisture-tight compartments and they are not handled directly by the user of the kit. The slide has two wells (5) and (5') for receiving the first or second milk sample. Prior to use, the slide is in the open position.

The reference lyophilised reaction media are standardised so that the resulting reference colouration corresponds to a reference concentration of progesterone which may be set at between about 1 and about 3 ng/ml (for example 2 ng/ml), below which concentration the cow is regarded as being in heat. For another female of another mammal species, this threshold value is adjusted.

In order to analyse the quantity of progesterone in the milk, the slide is immersed in some milk that has not undergone any prior treatment, so that the wells are filled with the first and second milk samples. For reasons of reliability of the test, it is preferable to use fresh milk at a temperature of from 20 to 39° C. which has not previously been refrigerated. Below 15° C., the catalytic reactions are slowed and the incubation time is longer. In addition, progesterone is a molecule with low stability in milk.

After immersion, the slide is moved so that (1) the well containing the first milk sample is located opposite the compartment containing the first lyophilised reaction medium, and (2) the well containing the second milk sample is located opposite the compartment containing the first reference lyophilised reaction medium. The kit is agitated for about 30 seconds so that said first media dissolve completely in their respective samples. The slide is then moved again so that (1) the well containing the first milk sample is located opposite the compartment containing the second lyophilised reaction medium, and (2) the well containing the second milk sample is located opposite the compartment containing the second reference lyophilised reaction medium. The kit is again agitated for about 30 seconds so that said second media in turn dissolve completely in their respective samples. The samples are then incubated for 3 to 5 minutes, and then the colouration obtained with the first sample is observed and compared with the reference colouration of the second sample. If the resulting pink colouration is more intense or equal to the reference colouration, the milk tested contains a progesterone concentration greater than 2 ng/ml and the cow is not in heat. By contrast, if the resulting pink colouration is less intense than the reference colouration, the tested milk contains a progesterone concentration less than 2 ng/ml and the cow is regarded as being in heat.

As an alternative, the progesterone kit comprises a well intended to receive the milk sample and two compartments containing respectively the two lyophilised reaction media required to perform the assay, each in a different compartment. Both compartments may be moved sequentially above the well to have the media contained in the compartment poured into the well. If a reference test is required, then the kit may comprise another set of well and compartments to perform the reference test.

The detection method according to the invention has a number of advantages.

The method enables highly accurate qualitative and semi-quantitative results to be obtained owing to the colour reaction induced by the immunoenzymatic method.

The method can be miniaturised and fully integrated in the form of a ready-to-use kit for single use which does not have to be stored at low temperature, the reaction media being lyophilised and very stable at ambient temperature.

The method is simple to use. When packaged in the form of a kit according to the invention, the method simply comprises adding the sample of medium to be tested to the compartments, diluting the lyophilised reaction media in said sample, and observing the colouration with the aid of a colour scale and/or by comparison with a reference colouration. The method can therefore be carried out by any person other than a person skilled in the art (technician). Accordingly, in the case of a method for detecting progesterone in cows' milk, the method can be carried out especially by the cattle breeder or the vet.

The method is rapid to use. The method does not require multiple washing and/or incubation steps. After addition of the sample and dilution of the lyophilised reaction media, the colour reaction can be observed within a few minutes, generally in less than 10 minutes. The incubation time will vary especially according to the nature of the medium to be tested, the kinetics of the enzymes used, the environmental conditions (temperature, etc.).

The method can be used in situ. When packaged in the form of a kit according to the invention, the method is designed for use at the very site at which the medium to be tested is taken.

The method permits the testing of media which can be obtained in only small volumes, especially sweat, lachrymal fluid and mucosal secretions.

The method is not used directly on the animal of which a biological medium is to be tested. The animal is therefore never in contact with the vector compounds and reaction compounds, which may be toxic, of which the device is composed.

The method according to the invention can be used to determine the cyclicity or gestational state of an animal or human female, especially a non-primate mammal, in particular a productive one, which comprises carrying out the detection method and analysing the progesterone in a biological medium taken from said animal or human.

The present invention will be better understood in the light of the following example, which is given by way of a non-limiting example of the invention and refers to the accompanying drawing in which:

FIG. 1 shows the kit according to the invention.

DESCRIPTION OF PREFERRED EMBODIMENTS

EXAMPLE

1. Obtainment of Anti-progesterone 2B5 Monoclonal Antibodies

Anti-progesterone 2B5 monoclonal antibodies of the IgG1 immunoglobulin type are produced by the cell line CNCM I-3403.

That cell line was obtained by fusion of B lymphocyte of the spleen of Balb/c albino mice and Sp2/Ag myeloma. The line was selected (1) by measuring the affinity of the antibodies produced for the FAD-P4 conjugate by the ELISA method with coating of the FAD-progesterone and (2) by measuring the affinity of the antibodies for P4 in free form by the competitive ELISA method with coating of the FAD-progesterone.

2. Preparation of Inactivated Apo-glucose Oxidase

Inactivation of the Catalase 500 ml of the solution GenencorOxy GO HPL 5000 (25.7 mg/ml of protein at A280 and 224,000 enzymatic units) are added to 1 liter of demineralised water. 6.0 g of sodium bisulfite are then added with stirring until dissolution is complete. The glucose oxidase solution (referred to hereinafter as GOD solution) is incubated for 24 hours at ambient temperature with gentle stirring.

The GOD solution is then treated by ultrafiltration and diafiltration using a 6 Ft$^2$, 10K PES membrane at ambient temperature. The membrane is cleaned beforehand with 0.1 N sodium hydroxide solution. The GOD solution is concentrated in a final volume of 500 ml in the course of 10 minutes. The solution is then subjected to diafiltration against 7 diavolumes of demineralised water and against 5 diavolumes of a 0.05 M sodium acetate solution, pH 4.5, for 2½ hours. A GOD solution of 830 ml is obtained, comprising 14.2 mg/ml of proteins (A280) and having an enzymatic activity of 2540 U/ml.

The GOD solution is then filtered using a Buchner funnel of fritted glass having a diameter of 9 cm and containing a filter paper loaded beforehand with 5 of C300. 830 ml of filtered GOD solution are collected. The pH of the solution is adjusted to 6 with a 1 N sodium hydroxide solution for a final volume of 853 ml.

A chromatography column 7.5 cm by 19 cm is packed with 730 ml of Sephacel DEAE resin and then equilibrated with a 0.05 M sodium acetate equilibrating solution, pH 6.0. The GOD solution (853 ml) is loaded onto the column and the column is rinsed with a volume of equilibrating solution. The sample is then eluted with a gradient of sodium acetate from 0.8 M, pH 6.0, 2.2 liters to 0.2 M, pH 3.5, 2.2 liters at a rate of elution of 20 ml/minute, and the eluate is collected in fractions. The ratio A450/A405 is then measured for each fraction, only the 6 fractions having a ratio greater than 1.55 being kept and combined. A solution (or pool) of GOD of 1100 ml is obtained.

With stirring, the pH of the solution is adjusted to 4.5 by addition of 10 ml of 2.0 N sodium hydroxide solution, and then the absorbance is measured at A280 and A450. The GOD solution has 10.4 g of protein and an enzymatic activity of 1785 U/ml. It is stored at from 2 to 8° C.

Stabilisation of the Glucose Oxidase

The GOD solution is divided into three portions treated separately with dimethyl adipimidate (referred to hereinafter as DMA). A GOD fraction of 367 ml is diluted with cold demineralised water, qs 2.5 liters. The pH is adjusted to 8.52 by addition of 1.58 M N-ethylmorpholine (referred to hereinafter as NEM).

5.5 g of DMA are dissolved in 13.75 ml of a 1.0 M potassium carbonate buffer solution, pH 9.5. The resulting DMA solution is added to the diluted GOD fraction with rapid stirring and over a period of 5 minutes. The pH of the resulting GOD solution is adjusted to 8.5 with the 1.58 M NEM solution. The buffered solution is stored at 4° C. for 4 hours. The other two fractions are treated in the same manner.

The treated fractions are concentrated and subjected to diafiltration in 50% glycerol using a 0.5 m$^2$ Biomax B-10A membrane, 10,000 MWCOS PES. The three fractions are added in succession. The fractions are subjected to diafiltration against 10 diavolumes of cold demineralised water and then 4 diavolumes of 50% glycerol. 560 ml of GOD solution at 18.5 mg/ml and 3700 U/ml are obtained and then stored at 5° C.

Inactivation of Apo-GOD 390 ml of a 50% glycerol solution, pH 4.0, comprising 10% w/v AMP are added to 560 ml of the crosslinked GOD solution, with stirring. The pH of the solution is adjusted to 1.65 by addition of 50% glycerol, pH 0.9, with rapid stirring. The solution is mixed at 2-8° C. for 20 minutes.

The GOD solution is concentrated and subjected to diafiltration using a Millipore 1.0 M$^2$ 10K PES membrane. The crosslinked GOD solution is concentrated to a volume of 675 ml and subjected to diafiltration with 2.7 ml of a solution of 50% glycerol/0.04 M AMP, pH 1.65, and 7 liters of a 50% glycerol solution, pH 1.65. 550 ml of apo-GOD solution having a protein concentration of 11.8 mg/ml and a residual enzymatic activity of 0.22 U/ml are obtained. When the FAD is added, the enzymatic activity is 1880 U/ml. This shows that the majority of the FAD has been removed from the apo-GOD solution. In addition, a A280/A260 ratio of 1.5 shows a residual amount of AMP.

The residual amounts of FAD and AMP are removed by adding to the crosslinked apo-GOD solution a paste comprising 2.4 g of dextran, 16 g of carbon in 40 ml of 0.2 M sodium phosphate, 50% glycerol pH 8.0. The pH is adjusted to 7 with 1 N sodium hydroxide solution. The suspension is stirred overnight at low temperature.

The dextran-carbon paste is centrifuged for 15 minutes at 16,000 g at 5° C. The slightly cloudy supernatant is harvested and filtered over 0.8, 0.45 and 0.2 μm filters. 540 ml of apo-GOD solution comprising 5.45 g of proteins are obtained.

In order to remove the glycerol and residual reagents, a 11.28×45 cm column packed with 4.5 liters of a Sephadex G25 resin is used. The elution flow rate is 40 ml/minute, and the column is equilibrated with Sephadex G-25 buffer containing 0.1 M sodium phosphate, 0.1% BSA and 5 mg/ml mannitol, pH 7.0. The apo-GOD is loaded onto the column and it is eluted with the Sephadex G-25 solution at low temperature. The fractions are collected when A280>0.5. A apo-GOD solution (or pool) of 1.2 liters is obtained, filtered using 0.2μ filters and lyophilised. 30.6 g of a white solid comprising 4.93 g of proteins and having a residual enzymatic activity of 0.008 U/mg are obtained.

3. Preparation of the FAD-progesterone Conjugate

FAD and/or its precursors are synthesised according to a reaction cascade which is well known to the person skilled in the art and has been widely documented. Accordingly, starting from inosine, it is possible to synthesise in cascade (1) 2',3',5'-tri-O-acetylinosine according to Bredereck et al., Chem Ber (1947) 40: 401-405, (2) 6-chloro-9-(2',3',5'-tri-O-acetyl-B-D-ribofuranosyl)purine according to Gerster et al. J Org Chem (1963) 28: 945-948, (3) 6-chloro-9-B-D-ribofuranosylpurine according to Brown et al. J Biol Chem (1953) 204: 1019-1024, (4) 6-chloro-9-B-D-ribofuranosyl purine-5'-phosphate and then N6-(6-aminohexyl)-adenosine-5'-monophosphate (AHAMP) according to Guilford et al. Chemica Scripta (1972) 2: 165-170, (5) N-trifluoroacetyl-AHAMP (N-TFA-AHAMP), (6) N-TFA-6-aminohexyl-FAD (TFA-AHFAD), (7) N6-(6-aminohexyl)-FAD (AHFAD), the AHFAD subsequently being used in the progesterone coupling reaction.

103 mg of P4-HNS (0.24 mmol) are dissolved in 1.5 ml of DMF, and the resulting solution is cooled on ice to −10° C. 27 μl of N-methylmorpholine 0.24 mmol (NMM) and then 32 μl of isobutyl chloroformate 0.24 mmol are then added, with vigorous stirring, in the course of several minutes.

In parallel, 108 mg of AHFAD (0.12 mmol) are dissolved in 10 ml of DMF/DMSO 1/1, the pH is adjusted to 8 with NMM, and the resulting solution is cooled on ice. The AHFAD solution is added slowly to the P4-NHS solution, and then 5 ml of water are added in order to dissolve the products completely.

After 90 minutes, a second aliquot of 103 mg of P4-HNS is activated by addition of 27 μl of NMM and 32 μl of isobutyl chloroformate and stirring at −10° C. for 4 minutes. The second aliquot of P4-NHS is then added to the P4-HNS solution. After three hours, the coupling reaction is stopped by addition of sodium bicarbonate. The resulting product is purified by preparative chromatography on a Delta-Pak C18 RCM 25×210 mm column (Waters) with a flow rate of 40 ml/min. A linear elution gradient is applied from 20% to 80% of solvent B, over 30 minutes (solvent A: 0.02M phosphate buffer, pH 5.5—solvent B: acetonitrile/phosphate buffer 1/1). The main fractions obtained between 17 and 19 minutes' elution are combined and concentrated using a rotary evaporator. The final product is finally dried by lyophilisation.

Analysis of the final product by spectrophotometry at 450 nm (E=11,300/M.cm) gives a conjugate content of 94.4 mg, corresponding to a yield of 60%. Chromatographic analysis by LC-MS (ion spray+) and UV confirms the identity of the conjugate with a Mr of 1296.7 (calculated Mr: 1297.3) and a Tr of 5.92 min., the chromatographic purity determined at 215 nm being greater than 90% s/s.

The operating conditions are as follows: Atlantis C18 column, 4.6×50 mm, 3 μm (Waters)—mobile phase: linear elution gradient from 5% to 65% solvent B in 10 minutes (solvent A: 0.05% trifluoroacetic acid in water, solvent B: acetonitrile)—Waters Alliance HT 2790 system coupled to a Waters ZQ4000 mass spectrometer and a Waters 996 PDA detector.

4. Preparation of the Lyophilised Reaction Media

A. Preparation of the Matrix Solutions

The matrix solutions are obtained by dissolving 25 g of trehalose, 75 g of mannitol, 25 g of dextran T40 and 5 g of bovine serum albumin in a 0.1 M sodium phosphate buffer, pH 7, qs 1 liter.

B. Preparation of the Stock Solutions of the Compounds

Stock solution of apo-glucose oxidase at 6 mg/ml (136 U) by dissolving lyophilised apo-glucose oxidase in the matrix solution.

Stock solution of glucose at 50 mg/ml.

Stock solution of anti-progesterone 2B5 antibodies at 2 mg/ml.

Stock solution of HRP at 5 mg/ml: 5 mg of HRP (Sigma) are dissolved in a 0.1 M sodium phosphate buffer solution, pH 7.0, qs 1 ml.

Stock solution of FAD-progesterone conjugate at 0.2 μM: 1.2 mg of FAD-P4 are dissolved in a 0.1 M sodium phosphate buffer solution, qs 1 ml. The molar concentration of the stock solution is determined by the ratio [absorbance at 450 nm/0.0113]. The stock solution is diluted so that the FAD-P4 is present in a final concentration of 0.2 μM.

Stock solution of chromogenic compound DHSA at 200 mM: dissolution of 53 mg of DHSA (Sigma) in 1 ml of distilled water.

Stock solution of 4-aminoantipyrine at 8 mM; 1.6 mg of 4-AP (Sigma) are dissolved in 1 ml of distilled water.

Stock solution of ascorbate oxidase at 200 U/ml by reconstitution of ascorbate oxidase (Sigma) in a 0.1 M sodium phosphate buffer solution, pH=7.

C. Preparation of the Mixtures 4 different mixtures are prepared starting from the stock solutions according to the quantities by volume detailed in Tables I and II below.

The four mixtures correspond to a first mixture (corresponding in fine to the first lyophilised reaction medium), a second mixture (corresponding in fine to the second lyophilised reaction medium), a first reference mixture (corresponding in fine to the first reference lyophilised reaction mixture) and a second reference mixture (corresponding in fine to the second reference lyophilised reaction medium).

TABLE I

Composition of the first mixture and of the first reference mixture expressed as the volume (microlitres) of the stock solutions used.

| | ApoGOD (μl) | 4-AP (μl) | Asc. Ox. (μl) | Ac. 2B5 (μl) | Matr. Sol. (μl) | Total volume |
|---|---|---|---|---|---|---|
| 1st medium | 11.00 | 3.375 | 1.75 | 0.110 | qs | 50.00 |
| 1st reference medium | 11.00 | 3.50 | 1.75 | None | qs | 50.00 |

TABLE II

Composition of the second mixture and of the second reference mixture expressed as the volume (microlitres) of the stock solutions used.

| | HRP (µl) | DHSA (µl) | FAD-P4 (µl) | Matr. Sol. (µl) | Total volume |
|---|---|---|---|---|---|
| 2nd medium | 0.30<br>1.5 µg | 1.887<br>100 µg<br>370 nmol | 4.6<br>1.19 ng<br>0.92 pmol | qs | 50 |
| 2nd reference medium | 0.30<br>1.5 µg | 1.887<br>100 µg<br>370 nmol | 1.88<br>0.45 ng<br>0.38 pmol | qs | 50 |

D. Preparation of the Solid Reaction Media

50 µl aliquots of the mixtures are immersed in a bath of liquid nitrogen, the aliquots immediately assuming the form of a spherical matrix.

E. Preparation of the Lyophilised Reaction Media

The moisture in the solid reaction media is sublimed by lyophilisation in vacuo and according to a temperature gradient comprising exposure in vacuo for 4 hours at −40° C. and then for 2.5 hours from −40° C. to −10° C., then for 3 hours at −10° C., then for 3 hours from −10° C. to +30° C., for 5 hours at 30° C. The 4 different lyophilised reaction media obtained and the mass quantities of reaction compounds are detailed in Tables III and IV below.

TABLE III

Composition of the first lyophilised reaction medium and of the first reference lyophilised reaction medium.

| | ApoGOD (µg) | 4-AP (µg) | Asc. Ox. (U) | Ac. 2B5 (ng) | Total vol. (µl) |
|---|---|---|---|---|---|
| 1st medium | 66<br>(1.5 U) | 5.4<br>(27 nmol) | 0.35 | 110 | 50 |
| 1st reference medium | 66<br>(1.5 U) | 5.6<br>(28 nmol) | 0.35 | None | 50 |

TABLE IV

Composition of the second lyophilised reaction medium and of the second reference lyophilised reaction medium.

| | HRP (µg) | DHSA (µg) | FAD-P4 (ng) | Total vol. (µ') |
|---|---|---|---|---|
| 2nd medium | 1.5 | 100<br>(370 nmol) | 1.19<br>(0.92 pmol) | 50 |
| 2nd reference medium | 1.5 | 100<br>(370 nmol) | 0.45<br>(0.38 pmol) | 50 |

5. Preparation of the Glucose

The glucose is not incorporated into the four lyophilised reaction media. 100 µl of the glucose stock solution (5 mg of glucose) are deposited in each of the two wells for receiving the first and second milk samples. Before the reaction medium is added, the water is evaporated passively from the glucose solution until the glucose crystallises in the bottom of the compartment.

6. Packaging of the Lyophilised Reaction Media in the Kit

Before the detection method is carried out, the four reaction media according to Example 4E are packaged in the kit according to the invention.

Said kit, shown in diagrammatic form in FIG. 1, has two parts each formed of two independent compartments and a well. The first part is used for carrying out the method proper, and the second part is used for carrying out the reference method.

The glucose is added to each well as described above. The first lyophilised reaction medium is added to one compartment of the first part, and the second lyophilised reaction medium is added to the other compartment. Likewise, the first reference lyophilised reaction medium is added to one compartment of the second part, and the second reference lyophilised reaction medium is added to the other compartment.

In order to carry out the detection method it is necessary to dilute said lyophilised reaction media in the sample of cows' milk. To that end, a sample of milk that has not undergone any prior treatment is added to each of the two wells. A mechanism is then actuated so that the two compartments and the well of each part are in communication with one another and the two lyophilised reaction media are diluted in the sample.

Results Obtained

The effectiveness of the method of detecting progesterone in cows' milk by observing the colouration with the naked eye is determined by comparison with the reference method "The Ridgeway Milk Progesterone Enzyme-Immuno-Assay" (referred to hereinafter as the Ridgeway method) marketed by Ridgeway Science Ltd. (Lydney, GL15 6QX, Gloucestershire, United Kingdom) and with a calorimetric method using reflecto-spectrophotometry (referred to hereinafter as the Minolta method).

The Ridgeway method is a quantitative immunoenzymatic method which allows the concentration of progesterone in cows' milk to be determined.

The method is carried out according to the protocols specified by the manufacturer.

When the progesterone concentration in the cow's milk is less than or equal to 2.0 ng/ml, the cow is in heat, By contrast, when the progesterone concentration in the cow's milk is greater than 2.0 ng/ml, the cow is not in heat.

The Minolta method is a quantitative method carried out using a Minolta reflecto-spectrophotometer which permits the measurement of the parameter Absolute $[(b-a)_{Test}]$ of the first and second lyophilised reaction media diluted in a first milk sample and of the parameter $Abs[(b-a)_{Ref}]$ of the first and second reference lyophilised reaction media in a second milk sample in accordance with the recommendations of the Commission Internationale de l'Eclairage [International Illumination Commission] (CIE) and of the users manual "Precise color communication—Color control from perception to instrumentation" (Minolta Co. Ltd. 9242-4830-92; AAKBJ 14 (1998) p. 59).

In order to carry out the method, 100 ml of a first milk sample are placed in a first well of a microplate. 5 mg of glucose are mixed with the sample. The mixture is placed in a second well containing the first lyophilised reaction medium according to Example 4.E. and is incubated for 30 seconds. The mixture is then placed in a third well containing the second lyophilised reaction medium according to Example 4.E. and is incubated for 5 minutes. The parameter $Abs[(b-a)_{Test}]$ is measured. In parallel, 100 µl of a second milk sample are placed in a first well of a microplate. 5 mg of glucose are mixed with the sample. The mixture is placed in a second well containing the first reference lyophilised reaction medium according to Example 4.E. and is incubated for 30 seconds. The mixture is then placed in a third well containing the second reference lyophilised reaction medium according to Example 4.E. and is incubated for 5 minutes. The parameter $Abs[(b-a)_{Ref}]$ is measured.

When the difference (denoted Δ in Table IV below) between the parameters Abs[(b−a)$_{Test}$] and Abs[(b−a)$_{Ref}$] is less than −1.5, the cow is in heat. By contrast, when the difference between the parameters is greater than −1.5, the cow is not in heat.

The Minolta method is used only for information.

The method of observation with the naked eye (referred to hereinafter as Naked eye) consists in comparing the test colouration obtained by dilution of the first and second lyophilised reaction media in a first milk sample and the reference colouration obtained by diluting the first and second reference lyophilised reaction media in a second milk sample.

The "Naked eye" method is carried out using a kit according to the invention.

When the intensity of the test colouration is less than that of the reference colouration (symbol< in Table V), the cow is considered to be in heat. By contrast, when the intensity of the test colouration is greater than or equal to that of the reference colouration (symbols >and =in Table V), the cow is not considered to be in heat.

The results obtained are then compared with those obtained by the Ridgeway method.

In order to obtain comparable results, the Ridgeway, Minolta and "Naked eye" methods are carried out concomitantly at the very site at which the milk sample is taken from the cows.

The milk of 95 cows is tested by the Ridgeway, Minolta and "Naked eye" methods. A comparison of the results obtained allows the sensitivity and specificity of the kit to be determined, as well as the positive and negative predictive values. The cows are in heat when the concentration of progesterone in the cows' milk measured by the Ridgeway method is less than or equal to 2 ng/ml. By contrast, the cows are not in heat when the concentration of progesterone in the cows' milk measured by the Ridgeway method is greater than 2 ng/ml.

The sensitivity of the kit corresponds to the number of positive tests (referred to hereinafter as true-positive) obtained by observation with the naked eye relative to the number of positive tests validated by the Ridgeway method.

The specificity of the kit corresponds to the number of true-negative tests obtained by observation with the naked eye relative to the number of negative tests validated by the Ridgeway method.

The positive predictive value of the kit corresponds to the probability of having a cow in heat when the test is positive, that is to say the number of true-positive tests relative to the number of positive tests obtained.

The negative predictive value of the kit corresponds to the probability of having a cow that is not in heat when the test is negative, that is to say the number of true-negative tests relative to the number of negative tests obtained.

As shown in Table V below, 17 tests are true-positive and 2 tests are false-negative. The kit according to the invention therefore has a sensitivity of 89.5%. In addition, 6 tests are false-positive and 70 tests are true-negative. The kit according to the invention therefore has a specificity of 92.1%. Accordingly, the kit has a positive predictive value of 73.9% and a negative predictive value of 97.2%.

The use of the kit according to the invention therefore makes it possible to identify the large majority of the cows in heat, and vice versa. The use of the reaction compounds in the form of lyophilised reactive media is therefore without consequence relative to a qualitative method. The kit according to the invention is therefore simple, reliable and rapid to use.

TABLE V

Determination of the state of the cows, in heat (P) or not in heat (N), by the Ridgeway, Minolta and "Naked eye" methods

| | Ridgeway [P4] ng/mL | State | Minolta Δ | State | Naked eye Col. | State | Comments |
|---|---|---|---|---|---|---|---|
| 1 | 16.6 | N | 2.50 | N | > | N | True negative |
| 2 | 20.0 | N | 3.30 | N | > | N | True negative |
| 3 | 20.0 | N | 2.97 | N | = | N | True negative |
| 4 | 16.0 | N | 2.72 | N | = | N | True negative |
| 5 | 8.8 | N | 2.24 | N | > | N | True negative |
| 6 | 0.0 | P | −4.70 | P | < | P | True positive |
| 7 | 3.1 | N | −4.00 | P | < | P | False positive |
| 8 | 1.1 | P | −2.90 | P | < | P | True positive |
| 9 | 19.6 | N | 0.82 | N | > | N | True negative |
| 10 | 14.9 | N | 1.06 | N | > | N | True negative |
| 11 | 16.4 | N | 1.15 | N | = | N | True negative |
| 12 | 20.0 | N | 0.18 | N | = | N | True negative |
| 13 | 18.2 | N | 1.17 | N | = | N | True negative |
| 14 | 20.0 | N | 2.85 | N | > | N | True negative |
| 15 | 18.7 | N | 1.98 | N | > | N | True negative |
| 16 | 10.1 | N | −0.60 | N | = | N | True negative |
| 17 | 20.0 | N | 3.24 | N | > | N | True negative |
| 18 | 0.0 | P | −4.10 | P | < | P | True positive |
| 19 | 20.0 | N | 3.13 | N | = | N | True negative |
| 20 | 0.0 | N | −0.10 | N | = | N | True negative |
| 21 | 20.0 | N | 1.60 | N | > | N | True negative |
| 22 | 18.9 | N | 2.04 | N | > | N | True negative |
| 23 | 20.0 | N | 1.68 | N | = | N | True negative |
| 24 | 20.0 | N | 3.38 | N | > | N | True negative |
| 25 | 14.2 | N | −1.00 | N | = | N | True negative |
| 26 | 0.0 | P | 2.62 | N | > | N | False negative |
| 27 | 2.3 | N | −5.00 | P | < | P | False positive |
| 28 | 9.4 | N | −0.90 | N | = | N | True negative |
| 29 | 6.8 | N | −2.90 | P | < | P | False positive |
| 30 | 20.0 | N | 2.21 | N | = | N | True negative |
| 31 | 12.3 | N | 0.49 | N | > | N | True negative |
| 32 | 14.2 | N | −0.10 | N | = | N | True negative |
| 33 | 20.0 | N | 6.02 | N | > | N | True negative |
| 34 | 10.5 | N | 4.76 | N | > | N | True negative |
| 35 | 20.0 | N | 6.55 | N | > | N | True negative |
| 36 | 20.0 | N | 3.21 | N | = | N | True negative |
| 37 | 6.3 | N | 0.18 | N | = | N | True negative |
| 38 | 8.0 | N | 2.46 | N | = | N | True negative |
| 39 | 2.1 | N | −2.20 | P | < | P | False positive |
| 40 | 0.9 | P | −4.60 | P | < | P | True positive |
| 41 | 9.4 | N | 3.52 | N | > | N | True negative |
| 42 | 20.0 | N | 2.78 | N | > | N | True negative |
| 43 | 0.0 | P | −5.3 | P | < | P | True positive |
| 44 | 1.5 | P | −3.1 | P | < | P | True positive |
| 45 | 10.7 | N | 1.73 | N | = | N | True negative |
| 46 | 15.3 | N | 2.48 | N | > | N | True negative |
| 47 | 10.2 | N | 6.46 | N | > | N | True negative |
| 48 | 15.0 | N | 3.25 | N | = | N | True negative |
| 49 | 16.1 | N | 0.18 | N | = | N | True negative |
| 50 | 9.1 | N | 3.16 | N | > | N | True negative |
| 51 | 20.0 | N | 4.29 | N | > | N | True negative |
| 52 | 10.4 | N | 2.82 | N | = | N | True negative |
| 53 | 20.0 | N | 4.57 | N | > | N | True negative |
| 54 | 12.5 | N | 3.52 | N | > | N | True negative |
| 55 | 0.0 | P | −3.90 | P | < | P | True positive |
| 56 | 3.0 | P | −5.40 | P | < | P | True positive |
| 57 | 0.0 | P | −5.30 | P | < | P | True positive |
| 58 | 20.0 | N | 3.29 | N | > | N | True negative |
| 59 | 20.0 | N | 5.39 | N | > | N | True negative |
| 60 | 2.3 | N | −0.70 | N | = | N | True negative |
| 61 | 2.0 | P | −3.60 | P | < | P | True positive |
| 62 | 12.6 | N | 3.36 | N | = | N | True negative |
| 63 | 9.1 | N | 4.32 | N | > | N | True negative |
| 64 | 20.0 | N | 4.50 | N | > | N | True negative |
| 65 | 20.0 | N | 1.83 | N | > | N | True negative |
| 66 | 14.5 | N | 2.96 | N | > | N | True negative |
| 67 | 18.0 | N | 3.62 | N | > | N | True negative |
| 68 | 6.3 | N | 9.03 | N | > | N | True negative |
| 69 | 5.6 | N | −2.20 | P | < | P | False positive |
| 70 | 1.96 | P | −0.60 | N | = | N | False negative |

TABLE V-continued

Determination of the state of the cows, in heat (P) or not in heat (N), by the Ridgeway, Minolta and "Naked eye" methods

| | Ridgeway [P4] | | Minolta | | Naked eye | | |
|---|---|---|---|---|---|---|---|
| | ng/mL | State | Δ | State | Col. | State | Comments |
| 71 | 1.3 | P | −3.60 | P | < | P | True positive |
| 72 | 18.5 | N | 3.79 | N | > | N | True negative |
| 73 | 3.1 | N | −1.90 | P | = | N | True negative |
| 74 | 0.0 | P | −6.70 | P | < | P | True positive |
| 75 | 6.2 | N | −3.40 | P | = | N | True negative |
| 76 | 0.0 | P | −2.90 | P | < | P | True positive |
| 77 | 19.6 | N | 2.70 | N | > | N | True negative |
| 78 | 12.3 | N | 4.32 | N | > | N | True negative |
| 79 | 6.0 | N | 5.31 | N | > | N | True negative |
| 80 | 20.0 | N | 2.67 | N | > | N | True negative |
| 81 | 20.0 | N | 4.99 | N | > | N | True negative |
| 82 | 6.6 | N | 4.58 | N | > | N | True negative |
| 83 | 20.0 | N | 4.76 | N | > | N | True negative |
| 84 | 18.3 | N | 3.83 | N | > | N | True negative |
| 85 | 9.4 | N | 5.98 | N | > | N | True negative |
| 86 | 20.0 | N | 3.66 | N | > | N | True negative |
| 87 | 3.6 | N | 2.92 | N | = | N | True negative |
| 88 | 1.8 | P | −6.70 | P | < | P | True positive |
| 89 | 0.0 | P | −2.70 | P | < | P | True positive |
| 90 | 19.1 | N | 4.09 | N | > | N | True negative |
| 91 | 1.3 | P | −3.60 | P | < | P | True positive |
| 92 | 20.0 | N | 3.17 | N | = | N | True negative |
| 93 | 5.1 | N | 0.57 | N | = | N | True negative |
| 94 | 1.1 | P | −4.50 | P | < | P | True positive |
| 95 | 2.8 | N | −2.40 | P | < | P | False positive |

The invention claimed is:

1. A method for the qualitative and semi-quantitative detection of a ligand in a sample medium comprising
    dissolving first and second lyophilized reaction media in the sample medium,
        i) the first lyophilized reaction medium comprising an inactivated apoenzyme, a monoclonal antibody, a cofactor for a chromogenic compound, and at least one neutralising compound and
        ii) the second lyophilized reaction medium comprising a second enzyme, a coupled chromogenic compound, and a conjugate formed by covalently bonding a prosthetic group to a ligand,
    wherein one or both of the first and second lyophilized reaction media further comprises a substrate,
    wherein the conjugate independently binds (a) the monoclonal antibody in a specific and competitive maimer and (b) the inactivated apoenzyme, via the prosthetic group, thereby activating the apoenzyme, and
    wherein a color reaction is obtained by catalysis of at least one substrate by the activated apoenzyme, to give at least one reagent activating the second enzyme, and the activated second enzyme degrades the chromogenic compound proportional to the quantity of reagent formed and, indirectly, proportional to the quantity of the ligand present in the sample medium,
    incubating the sample medium in order to carry out an immunoenzymatic method, and
    observing the resulting coloration.

2. The method according to claim 1, wherein the resulting coloration is observed with the naked eye.

3. The method according to claim 1, wherein the lyophilized reaction media are obtained by
    mixing reaction compounds with a matrix solution comprising at least one vector compound,
    forming solid reaction media by immersing volumes of the mixture in liquid nitrogen, and
    forming lyophilized reaction media by sublimation of the solid reaction media by lyophlisation in vacuo.

4. The method according to claim 3, wherein the vector compound is a glucidic compound.

5. The method according to claim 4, wherein the glucidic compound is selected from the group consisting of simple and complex soluble sugars.

6. The method according to claim 4, wherein the glucidic compound is selected from the group consisting of monosaccharides and polysaccharides.

7. The method according to claim 3, wherein the vector compound is selected from the group consisting of trehalose, mannitol, dextran and bovine serum albumin.

8. The method according to claim 4, wherein the glucidic compound is a glucose polymer.

9. The method according to claim 3, wherein the vector compounds represent from 65 to 95% by volume of the lyophilized reaction media.

10. The method according to claim 1, wherein the dissolving of the lyophilized reaction media in the sample medium is simultaneous.

11. The method according to claim 1, wherein the dissolving of the lyophilized reaction media in the sample medium is sequential.

12. The method according to claim 1, further comprising carrying out a reference method by
    dissolving at least one reference lyophilized reaction medium without monoclonal antibodies, in a second sample medium,
    incubating the second sample medium,
    observing the resulting reference coloration, and optionally
    comparing the reference coloration and the coloration obtained with the sample medium.

13. The method according to claim 12, wherein the resulting reference coloration corresponds to a given concentration of the ligand.

14. The method according to claim 12, wherein the reference method comprises at least two different reference lyophilized reaction media,
    first reference lyophilized reaction medium comprising the inactivated apoenzyme, the cofactor for the chromogenic compound, and at least one neutralising compound and
    second reference lyophilized reaction medium comprising the second enzyme, the coupled chromogenic compound, and the conjugate,
    wherein one or both of the first and second reference lyophilized reaction media further comprises a substrate.

15. The method according to claim 1, wherein the sample medium is a biological medium.

16. The method according to claim 15, wherein the biological medium is taken from an animal or from a human being.

17. The method according to claim 16, wherein the animal is a companion animal.

18. The method according to claim 15, wherein the biological medium is selected from the group consisting of saliva, milk, urine, sweat, lachrymal fluid, mucosal secretions, plasma, amniotic fluid, cerebro-spinal fluid, water, and serum.

19. The method according to claim 18, wherein the biological medium is milk.

20. The method according to claim 1, wherein the ligand is selected from the group consisting of haptens, peptides, oligopeptides and polypeptide fragments protein fragments, glycoproteins, lipoproteins and steroids.

21. The method according to claim 1, wherein the ligand belongs to the class selected from the group consisting of antigens, hormones, vitamins, metabolites and antibiotics.

22. The method according to claim 21, wherein the ligand is progesterone in free form.

23. The method according to claim 1, wherein the apoenzyme is an oxidase that catalyses the substrate in the presence of the prosthetic group to produce at least one hydrogen peroxide.

24. The method according to claim 23, wherein the apoenzyme is apoglucose oxidase, the prosthetic group is flavin adenine dinucleotide and the substrate is glucose.

25. The method according to claim 1, wherein the second enzyme is horseradish peroxidase and the chromogenic compound is 5-dichloro-2-hydroxybenzenesulfonate coupled to 4-aminoantipyrine.

26. The method according to claim 1, wherein the ligand is progesterone in free form in milk.

27. The method according to claim 1, wherein the monoclonal antibody is an anti-progesterone 2B5 antibody produced by the cell line deposited on 17 Mar. 2005 with the Collection Nationale des Cultures de Microorganismes (National Microorganism Culture Collection) under number I-3403.

28. The method according to claim 1, wherein the neutralising compound is ascorbate oxidase.

29. The method according to claim 22, wherein the reference coloration corresponds to a concentration of between 1 and 3 ng/ml of progesterone in female mammals' milk.

30. The method according to claim 29, wherein the female mammal is a cow.

31. The method according to claims 29, wherein the reference coloration corresponds to a concentration of 2 ng/ml of progesterone in cows' milk.

\* \* \* \* \*